US012687537B2

(12) United States Patent  
Oduro

(10) Patent No.: US 12,687,537 B2  
(45) Date of Patent: Jul. 21, 2026

(54) SYSTEMS AND METHODS TO ASSESS AND REDUCE SALT LEVELS IN A MRU

(71) Applicant: Saudi Arabian Oil Company, Dhahran (SA)

(72) Inventor: Harry Daniel Oduro, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 428 days.

(21) Appl. No.: 18/351,994

(22) Filed: Jul. 13, 2023

(65) Prior Publication Data

US 2025/0020626 A1 Jan. 16, 2025

(51) Int. Cl.
| | |
|---|---|
| G01N 33/28 | (2006.01) |
| B01D 61/24 | (2006.01) |
| C10L 3/10 | (2006.01) |

(52) U.S. Cl.
CPC ..... G01N 33/2835 (2013.01); B01D 61/2461 (2022.08); B01D 2325/0283 (2022.08)

(58) Field of Classification Search
CPC ............ G01N 33/2835; B01D 61/2461; B01D 2325/0283; B01D 2317/02; C07C 29/76; C07C 29/80; C07C 29/86; C10L 3/107
See application file for complete search history.

(56) References Cited

U.S. PATENT DOCUMENTS

| | | | |
|---|---|---|---|
| 2,787,326 A * | 4/1957 | Hughes | .................. C09K 8/528 |
| | | | 507/927 |
| 2005/0072663 A1 | 4/2005 | Laborie et al. | |

| | | | |
|---|---|---|---|
| 2013/0118989 A1 | 5/2013 | Caires Fernandez | |
| 2017/0015612 A1 | 1/2017 | Bussell et al. | |
| 2018/0037805 A1* | 2/2018 | Utschig-Samuels | ..... C11D 3/10 |

FOREIGN PATENT DOCUMENTS

| | | |
|---|---|---|
| WO | WO 2007073204 | 6/2007 |
| WO | WO 2009017971 | 2/2009 |
| WO | WO 2010080038 | 7/2010 |
| WO | WO 2011028131 | 3/2011 |
| WO | WO 2015198212 | 12/2015 |
| WO | WO 2020104004 | 5/2020 |
| WO | WO 2022155584 | 7/2022 |

OTHER PUBLICATIONS

Brustad et al., "Hydrate Prevention using MEG instead of MeOH: Impact of experience from major Norwegian developments on technology selection for injection and recovery of MEG," Prepared for presentation at the 2005 Offshore Technology Conference held in Houston, TX, May 2-5, 2005, 10 pages.

Haghighi et al., "Experimental and thermodynamic modelling of systems containing water and ethylene-glycol: Application to flow assurance and gas processing," Fluid Phase Equilibria, 2009, 36 pages.

Koh et al., "Mechanisms of gas hydrate formation and inhibition," Fluid Phase Equilibria, Mar. 30, 2002, 194-197:143-151, 9 pages.

(Continued)

*Primary Examiner* — Pranav N Patel

(74) *Attorney, Agent, or Firm* — Fish & Richardson P.C.

(57) ABSTRACT

The disclosure relates to systems and methods to assess and reduce salt levels in a monoethylene glycol (MEG) recovery unit (MRU).

15 Claims, 16 Drawing Sheets

(56)                    References Cited

OTHER PUBLICATIONS

Mokhatab et al., "A Review of Strategies for Solving Gas-Hydrate Problems in Subsea Pipelines," Energy Sources, Part A: Recovery, Utilization and Environmental Effects, Jan. 2007, 29:39-45, 7 pages.
Sami et al., "Gas Hydrate Applications and Problems in Oil and Gas Industry," International Journal of Scientific & Engineering Research, Aug. 2013, 4(8):1-5, 5 pages.
Teixeira et al., "Offshore Monoethylene Glycol Recovery Units: The Importance of Choice of MEG State in the Reference Environment for Effective Exergy Analysis," Prepared for presentation at the Offshore Technology Conference Brasil held in Rio de Janeiro, Brazil, Oct. 27-29, 2015, 10 pages.
Zarinabadi et al., "Problems of Hydrate Formation in Oil and Gas Pipes Deals," Australian Journal of Basic and Applied Sciences, Dec. 2011, 5(12): 741-745, 5 pages.
International Search Report and Written Opinion in International Appln. No. PCT/US2024/037211, mailed on Nov. 13, 2024, 14 pages.
Odeigah et al., "Regeneration and Reclamation of Mono-Ethylene Glycol (MEG) Used as a Hydrate Inhibitor: A Review," American Journal of Chemical Engineering, Apr. 14, 2022, 10(2):32-45, 14 pages.

* cited by examiner

| MEG Salt Analyses | Wellhead Formation Water | Rich MEG Inlet Section MRU | Rich MEG Regeneration Section MRU | Lean MEG Reclamation Section MRU |
|---|---|---|---|---|
| Salt Evaporation | | | | |
| Gravimetric Analyses (mg/L) | Salt Undersaturation | 50,370 ± 213 | 111,735 ± 213 | 159,010 ± 213 |
| Semi-quantitative XRD (Identified Salts) (wt%) | N/D | Halite (NaCl) = 86wt% Sylvite (KCl) = 13wt% Sodium Sulfate (Na₂SO₄) = 3wt% Manganite (SiO₂) = 1wt% | Halite (NaCl) = 72wt% Sylvite (KCl) = 20wt% Barite (BaSO₄) = 4wt% Anhydrite (CaSO₄) = 2wt% Sodium Sulfate (Na₂SO₄) = 1wt% Albite (Na, Ca)(Si, Al)₄O₈ = 1wt% | Halite (NaCl) = 97.5wt% Sylvite (KCl) = 2.5wt% |
| ESEM | N/D | | | |

FIG. 7

SYSTEMS AND METHODS TO ASSESS AND REDUCE SALT LEVELS IN A MRU

FIELD

The disclosure relates to systems and methods to assess and reduce salt levels in a monoethylene glycol (MEG) recovery unit (MRU).

BACKGROUND

Gas hydrates can form in natural gas transportation and production systems, which can reduce or block the flow of gas. Hydrate inhibitors, such as MEG or methanol, can be injected into the wellhead to reduce (e.g., prevent) hydrate formation during production. The hydrate inhibitor can be removed from the produced gas and regenerated, for example, with a MRU.

SUMMARY

The disclosure relates to systems and methods to assess and reduce salt levels in a MRU. The systems and methods can detect and curb abnormal levels of total dissolved solids (TDS) and salt build-up in MRUs. Such abnormal levels of TDS and salt build-up in a MRU can adversely influence the process safety by fouling downstream pipelines, causing periodic system shutdowns in hydrate dominated natural gas processing units. The systems and methods include flushing the MRU with certain solutions and/or the use of a dual multi-cascade filtration system in the MRU.

The systems and methods of the disclosure can detect and reduce dissolved solids and salts from formation water in MRUs, thereby reducing (e.g., preventing) issues with MEG treatment and regeneration related to relatively high TDS levels and salt deposits. For example, the systems and methods can reduce (e.g., prevent) reductions in gas hydrate removal capacity, corrosion, erosion and/or system shutdowns associated with salt deposits and/or relatively high dissolved solid levels.

The systems and methods of the disclosure can be more efficient and/or more cost effective in the management and prevention of salt deposition in MRUs as well as in the regeneration of MEG than certain other methods for the management and prevention of salt deposition in MRUs and regeneration of MEG.

In a first aspect, the disclosure provides a method that includes: measuring a total dissolved solid content in a MEG-containing stream output from a MRU; comparing the measured total dissolved solid content to a threshold value; and when the measured total dissolved solid content is above the threshold value, flushing the MRU with a first solution including sodium bicarbonate and having a pH of from 4.8 to 5.3.

In some embodiments, the first solution includes from 0.015 M to 0.1 M sodium bicarbonate.

In some embodiments, a temperature of the first solution is from 35° C. to 50° C. In some embodiments, the method further includes flushing the MRU with the first solution a second time.

In some embodiments, the method further includes, after flushing the MRU with the first solution, flushing the MRU with a second solution having a pH of from 6.5 to 10.3. In some embodiments, the method further includes flushing the MRU with the second solution a second time.

In some embodiments, the method further includes, prior to flushing the MRU with the first solution, mechanically removing a salt deposit from a surface of the MRU and/or a flow line in fluid communication with the MRU.

In some embodiments, measuring the total dissolved solid content includes measuring concentrations of barium ($Ba^{2+}$), calcium ($Ca^{2-}$), strontium ($Sr^{2+}$), magnesium ($Mg^{2-}$), sodium ($Na^+$), potassium ($K^+$), sulfate ($SO_4^{2-}$), chloride ($Cl^-$), and carbonate ($CO_3^{2-}$) output from the MRU.

In some embodiments, the threshold value is at least 15700 mg/L.

In some embodiments, the method further includes: passing a MEG-containing stream output from a pretreatment section of the MRU through a first thermal cyclic filter, a first porous membrane filter, a second porous membrane filter and a third porous membrane filter to form a filtered stream; and inputting the filtered stream into the regeneration section of the MRU. The first porous membrane filter is downstream of the first thermal cyclic filter, the second porous membrane filter is downstream of the first porous membrane filter, and the third porous membrane filter is downstream of the second porous membrane filter.

In some embodiments, the first porous membrane filter has a first pore size, the second porous membrane filter has a second pore size, the third porous membrane filter has a third pore size, the first pore size is larger than the second pore size, and the second pore size is larger than the third pore size.

In some embodiments, the method further includes a second thermal cyclic filter and a third thermal cyclic filter. The second thermal cyclic filter is upstream of the second porous membrane filter and downstream of the first porous membrane filter, and the third thermal cyclic filter is upstream of the third porous membrane filter and downstream of the second porous membrane filter.

In a second aspect, the disclosure provides a method that includes flushing a MRU with a first solution including sodium bicarbonate and a pH of 4.8 to 5.3 at a temperature of 35° C. to 50° C.

In some embodiments, the method further includes, after flushing with the first solution, flushing the MRU with a second solution including a pH of 6.5 to 10.3.

In some embodiments, the method further includes, prior to flushing the MRU with the first solution, mechanically removing a salt deposit from a surface of the MRU and/or a flow line in fluid communication with the MRU.

In a third aspect, the disclosure provides a system that includes a pretreatment section configured to: i) receive a first stream including MEG and impurities including salt, water and hydrocarbons; ii) reduce an amount of hydrocarbons of the first stream to form a second stream having a reduced hydrocarbon content; and iii) output the second stream; a filtration section configured to: i) receive the second stream; ii) reduce an amount of one or more impurities in the second stream to form a third stream having a reduced impurity content; and iii) output the third stream; a reclamation section configured to: i) receive the third stream; ii) reduce an amount of salt in the third stream to form a fourth stream having a reduced salt content; and iii) output the fourth stream; and a regeneration section configured to: i) receive the fourth stream; ii) reduce an amount of water in the fourth stream to form a fifth stream having a reduced water content; and iii) output the fifth stream. The filtration section includes a first thermal cyclic filter, a first porous membrane filter downstream of the first thermal cyclic filter, a second porous membrane filter downstream of the first porous membrane filter, a third porous membrane filter downstream of the second porous membrane filter, and a first vacuum pump configured to maintain the filtration section at a first pressure.

In certain embodiments, the filtration section further includes: a second thermal cyclic filter upstream of the second porous membrane filter and downstream of the first porous membrane filter; and a third thermal cyclic filter is upstream of the third porous membrane filter and downstream of the second porous membrane filter.

In certain embodiments, the first porous membrane filter has a first pore size, the second porous membrane filter has a second pore size, the third porous membrane filter has a third pore size, the first pore size is larger than the second pore size, and the second pore size is larger than the third pore size. In certain embodiments, the first pore size is 50 μm to 100 μm, the second pore size is 5 μm to 50 μm, and the third pore size is 0.1 μm to 45 μm.

In certain embodiments, the filtration section further includes a first section and a second section. The first thermal cyclic filter, the first porous membrane filter, the second thermal cyclic filter and the second porous membrane filter are disposed in the first section. The first vacuum pump maintains the first section under the first pressure. The third thermal cyclic filter and the third porous membrane filter are disposed in the second section. A second vacuum pump maintains the second section under a second pressure.

BRIEF DESCRIPTION OF FIGURES

FIG. 7 depicts a table of experimental results.

DETAILED DESCRIPTION

Monoethylene Glycol Recovery Unit

Figure 1:
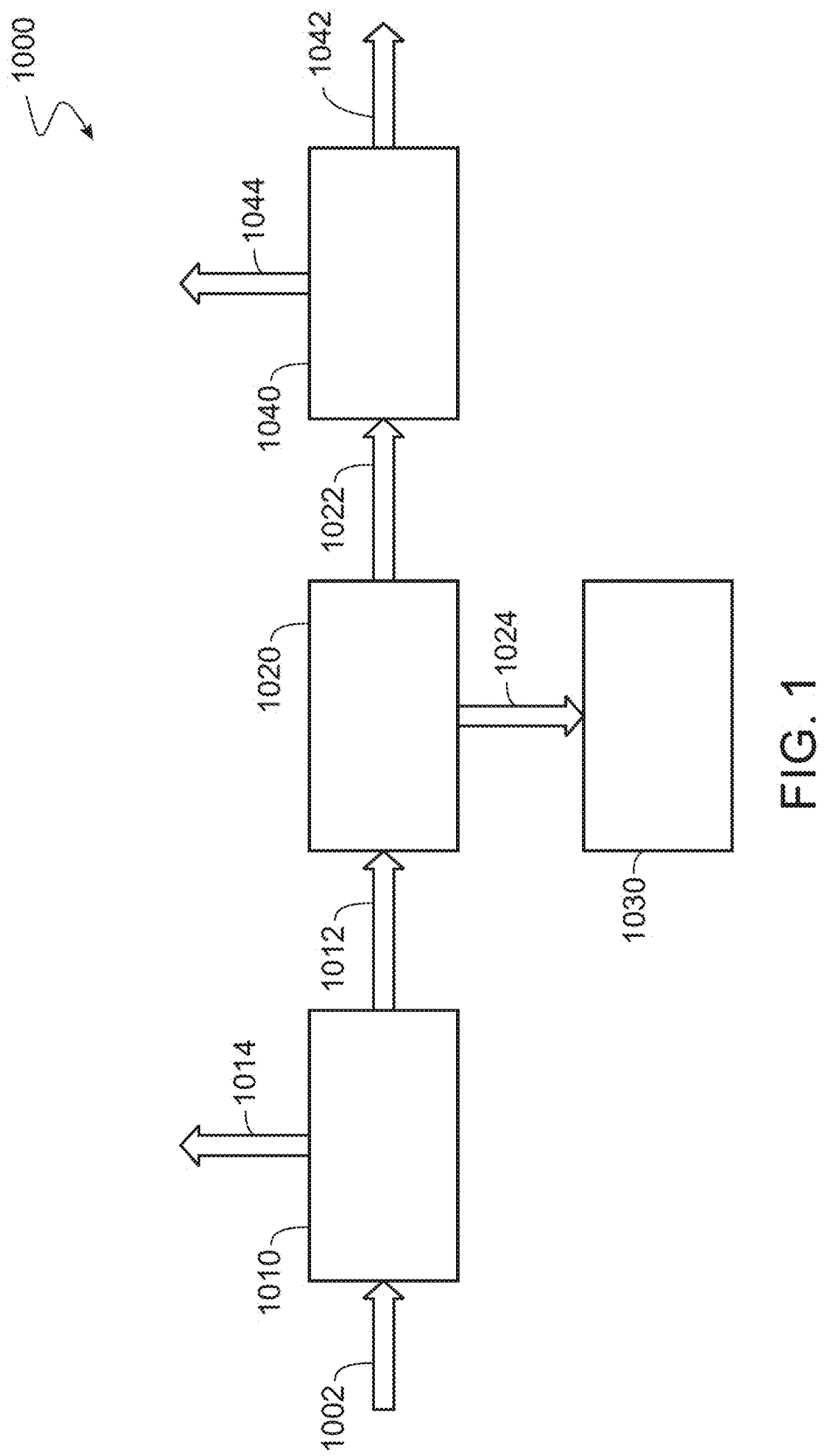
FIG. 1 depicts a schematic of a system.

FIG. 1 depicts a MRU 1000, which can be used to isolate MEG present in a rich MEG stream 1002. The rich MEG stream 1002 contains MEG, formation water, salt and hydrocarbons.

The rich MEG stream 1002 enters a pretreatment section 1010. In the pretreatment section 1010, the rich MEG stream 1002 is heated to separate the hydrocarbons from the rich MEG stream 1002 to form a stream 1012. The hydrocarbons can be removed from the pretreatment section 1010 as a stream 1014.

The stream 1012, which contains MEG, water and salt exits the pretreatment section 1010 and enters the reclamation section 1020. In the reclamation section 1020, the stream 1022 is heated to vaporize the MEG and a portion of the water, forming a stream 1022 containing the MEG and water and a stream 1024 containing salts in an aqueous liquid phase. The stream 1024 is sent to a salt management system 1030, where the salts can be collected by centrifugation or filtration and disposed.

The stream 1022 containing the vaporized MEG and water exits the reclamation section 1020 and enters the regeneration section 1040. In the regeneration section 1040, MEG and water are separated using distillation, such as with a vacuum fractionation tower. The water exits the regeneration section 1040 as the stream 1044. A lean MEG stream 1042 is recovered from the regeneration section 1040.

In some embodiments, the rich MEG stream 1002 includes at least 20 (e.g., at least 25, at least 30, at least 35) wt. % and/or at most 40 (e.g., at most 35, at most 30, at most 25) wt. % MEG. In some embodiments, the lean MEG stream 1042 includes at least 40 (e.g., at least 45, at least 50, at least 55) wt. % and/or at most 60 (e.g., at most 55, at most 50, at most 45) wt. % MEG.

Assessment Methods

Figure 2A:
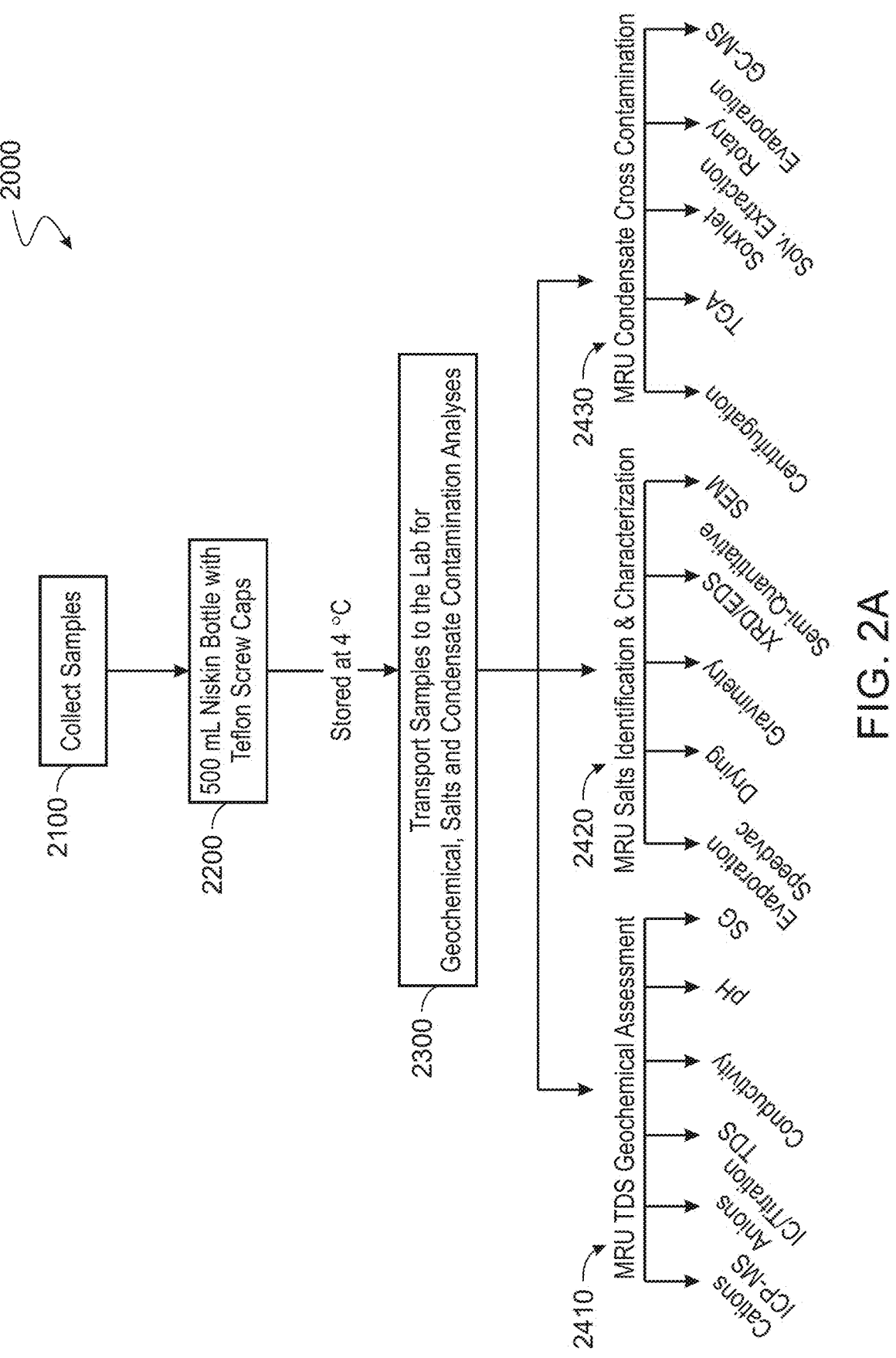
FIG. 2A depicts a flowchart of a method.

FIG. 2A depicts a flowchart of a method 2000 to monitor and identify the initial accumulation of salt debris or contaminants and sources of TDS, composition of salts, and condensate cross-contamination in the MRU 1000. Based on the results of the method 2000, a treatment method and/or a dual multi-cascade filtration system can be employed to reduce TDS levels in the MRU 1000 (see discussion below).

In a step 2100 the produced gas from the wellhead, the rich MEG stream 1002, the stream 1012, the stream 1022, the lean MEG stream 1042, and/or a bottom-hole water sample are sampled.

In step 2200, the samples from the step 2100 are disposed in 500 mL pre-cleaned borosilicate or plastic Niskin bottles with no headspace. The screw caps are cleaned with tissue to remove sample and/or salt particles adhering to the bottle threads that may affect the seal. The sample bottles are capped with a Teflon-lined cap and placed in a cooler with ice or dry ice to maintain a relatively low temperature. In some embodiments, the temperature is maintained at 0 (e.g., 1, 2, 3, 4° C.) to 5 (e.g., 4, 3, 2, 1° C.) In some embodiments, the temperature is maintained at 4° C.

In certain embodiments, for pressurized wellhead and bottom-hole water sampling, a sampling system using a nickel-coated stainless steel lecture bottles (Swagelock) equipped with multiple connectors and safety device is used in the step 2200 to avoid relatively high-pressure samples from breaking the sample bottle.

In step 2300, the samples are transported to a laboratory for further geochemical analysis. Without wishing to be bound by theory, it is believed that problems with sample withdrawal, transportation, collection and handling can result in sources of errors in the results.

The step 2100 can include rapid condensation and cooling, pressure reduction, and process indicators, as well as safety devices to protect online instruments and plant personnel. The method 2000 may include the collection of duplicate samples.

In step 2410, a geochemical assessment of the total dissolved solids (TDS) of the samples (e.g., the MRU samples) is performed. The step 2410 can include measuring cations by inductively coupled plasma mass spectrometry (ICP-MS), measuring anions by ion chromatography (IC) and/or titration, calculating TDS levels, measuring conductivity, measuring the pH and/or measuring the specific gravity.

The cations can include barium ($Ba^{2+}$), calcium ($Ca^{2+}$), strontium ($Sr^{2+}$), magnesium ($Mg^{2+}$), sodium ($Na^+$) and potassium ($K^+$). The anions can include sulfate ($SO_4^{2-}$), chloride ($Cl^-$) and hydroxide ($OH^-$), which can be measured by IC, and $CO_3^{2-}$ and $HCO_3^-$, which can be analyzed by chemical titration. TDS levels can be calculated from the sum of the chemical charge balance of cations and anions present in each sample.

In step 2420, salts present in the samples (e.g., the MRU samples) are identified and characterized to provide a structural characterization of the salt contaminants. The step 2420 can include evaporation and drying, followed by gravimetric analysis of the evaporated and dried samples. The evaporation can be performed using a speedvac that uses centrifugation, vacuum and elevated temperature to remove water to concentrate the salt while maintaining its integrity. In certain embodiments, the speedvac is operated at a temperature of at least 50 (e.g., at least 55, at least 60, at least 65, at least 70)° C. and/or at most 75 (e.g., at most 70, at most 65, at most 60, at most 55° C.) In certain embodiments, the speedvac is operated at a temperature of 75° C. The drying can be performed in an oven. In certain embodiments, the drying is performed at a temperature of at least 45 (e.g., at least 46, at least 47, at least 48, at least 49° C.) and/or at most 50 (e.g., at most 49, at most 48, at most 47, at most 46° C.) In certain embodiments, the drying is performed for at least 24 (e.g., at least 30, at least 36, at least 42) hours and/or at most 48 (e.g., at most 42, at most 36, at most 30) hours. In certain embodiments, the drying is performed at a temperature of 47° C. overnight.

Alternatively or additionally, the step 2420 can include characterization of the salts by semi-quantitative X-ray powder diffraction (XRD), energy-dispersive X-ray spectroscopy (EDS), and/or environmental scanning electron microscopy (ESEM).

Without wishing to be bound by theory, it is believed that the step 2420 can allow for the identification of the source of salts present in MRU samples. Examples of the source of salts include formation water, chemical dosing materials, and suspended or degraded corrosion products.

In the step 2430, a condensate cross contamination assessment is performed. Condensate cross contamination is a relatively common problem in MRUs caused by the interaction of suspended inorganic salt particles with heavier hydrocarbons or condensates leading to formation of sludge products. Without wishing to be bound by theory, it is believed that the sludge products can restrict the flow of gas. The degree of risk posed by hydrocarbon sludge products depends on the amount and composition of free hydrocarbon or organic components in the precipitated salt products. The causes and sources of these products should be understood to properly manage condensate cross contamination.

During normal, routine operations detailed TDS geochemical assessment (step 2410), salt identification and characterization (step 2420), and condensate cross contamination assessment (step 2430) may not all be performed. In some embodiments, only conductivity is measured as a guide to TDS measurement for normal, routine operations. In some embodiments, only TDS geochemical assessment (step 2410) is performed. Other combinations of one or more of steps 2410, 2420 and/or 2430 are possible.

Without wishing to be bound by theory, it is believed that failure to control excessive salt formation in the MRU can cause the aggregation and build-up of salts in the MEG-containing streams, thereby reducing the gas hydrate removal capacity, causing corrosion and erosion issues, and/or generating excessive salt deposits leading to periodic system shutdowns and downtimes to the natural gas plant.

Figure 2B:
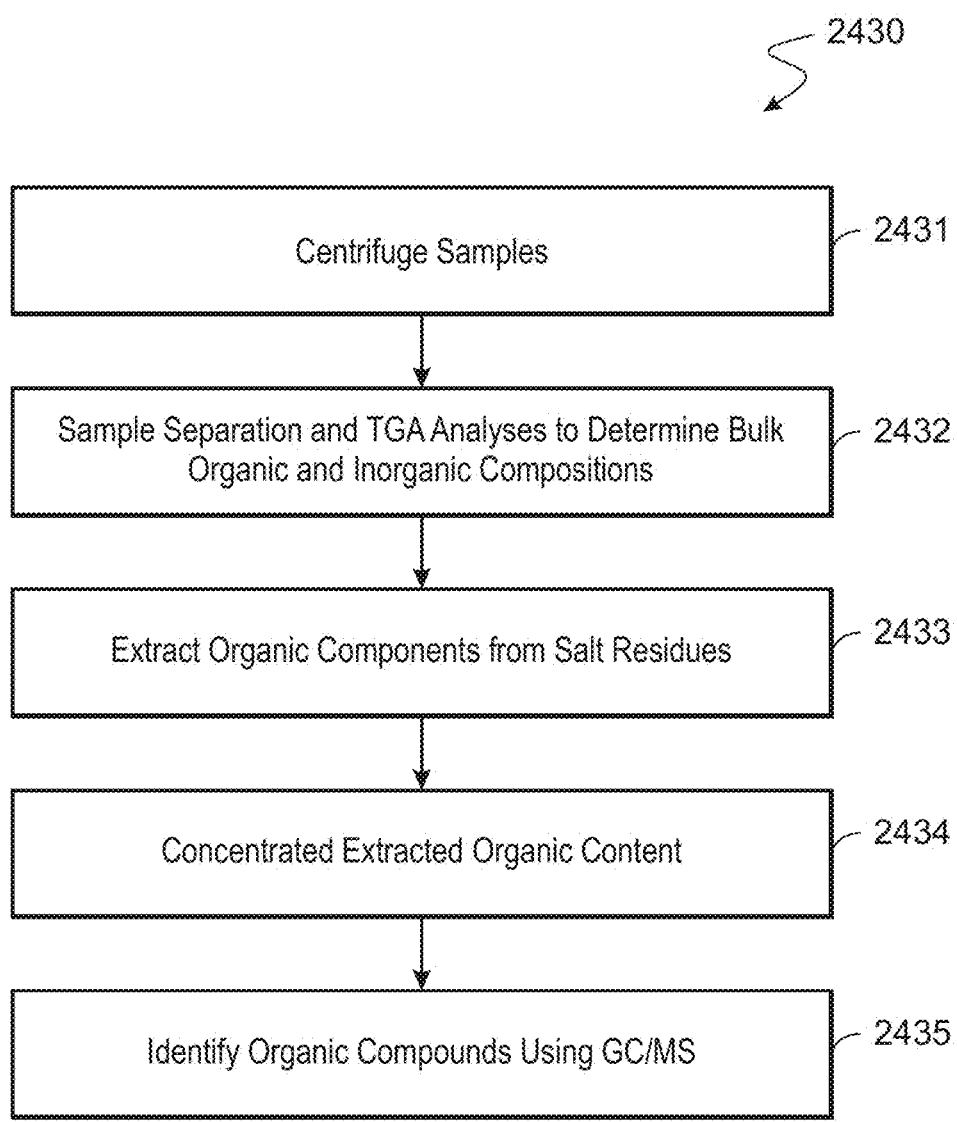
FIG. 2B depicts a flowchart of a method.

FIG. 2B depicts a schematic for the step 2430. In step 2431, the sample is centrifuged. In step 2432, the salt-containing hydrocarbon residues are collected and thermogravimetric analysis (TGA) is performed to determine the bulk organic and inorganic components.

In step 2433, a sub-sample of the salt-containing hydrocarbon residues is placed in a continuous soxhlet extraction system to extract the organic components using an appropriate solvent. Examples of the solvent include dichloromethane (DCM), chloroform, toluene and ethylbenzene. In some embodiments, the extraction is performed for at least 70 (e.g., at least 71) hours and/or at most 72 (e.g., at most 71) hours. In some embodiments, the extraction is performed at a temperature of at least 50 (e.g., at least 51, at least 52, at least 53, at least 54° C.) and/or at most 55 (e.g., at most 54, at most 53, at most 52, at most 51° C.) In some embodiments, the extraction is performed for 72 hours at a temperature of 55° C. Other reflux extraction methods may also be used to extract the organic components.

In step 2434, the organic content extracted with solvent (e.g., DCM) is concentrated (e.g., via rotary evaporation or under a nitrogen stream on a heating mantle).

In step 2435, gas chromatography coupled with mass spectrometry (GC-MS) is used to identify the organic components. Alternatively or additionally, GC coupled Thermogravimetric Analyzer with Fourier Transform Infrared-Mass Spectrometer (TGA-FTIR-MS) can be used.

The method 2000 allows for the identification of elevated TDS levels which can cause excessive salt buildup (salting, fouling) in the MRU.

In certain embodiments, the method 2000 is performed biweekly or weekly to monitor TDS and salt levels in the MRU 1000. In certain embodiments, the method 2000 is performed weekly to monitor TDS and salt levels in the MRU 1000. In certain embodiments, the method 2000 is performed biweekly to monitor TDS and salt levels in the MRU 1000. Typically, the frequency is selected based on the amount or levels of TDS, contaminants, and the amount of natural gas produced per day.

Treatment Methods

Figure 3:
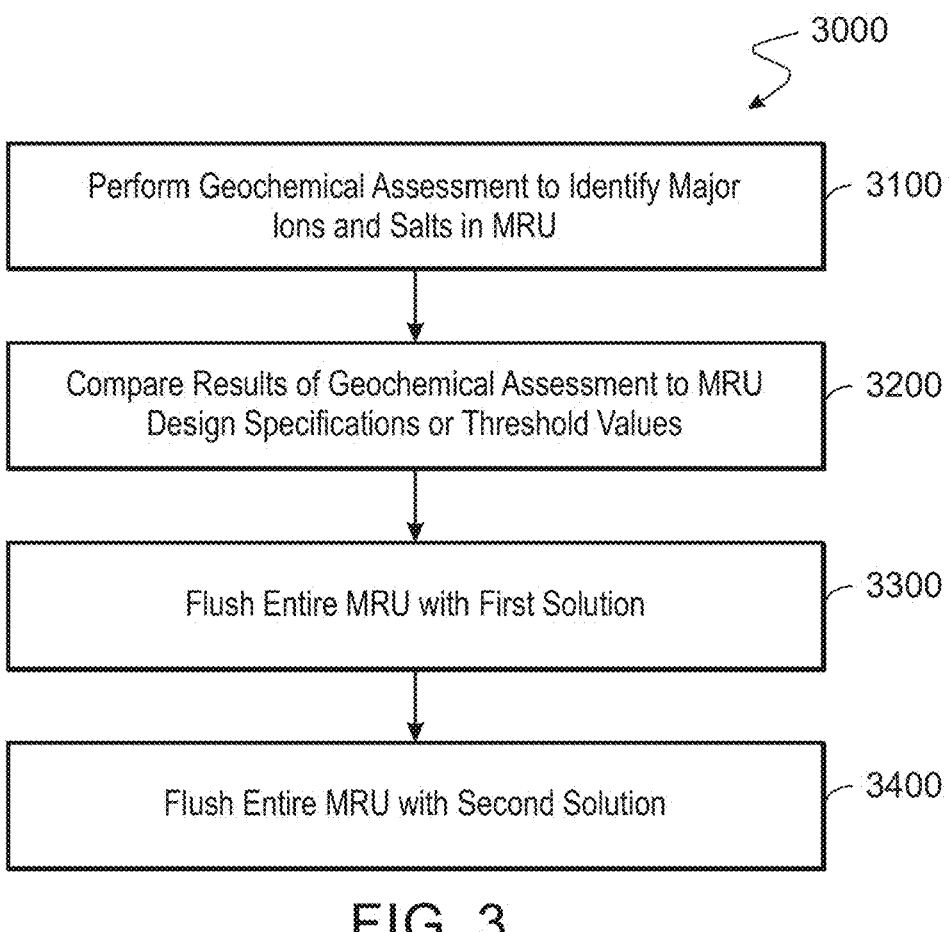
FIG. 3 depicts a flowchart of a method.

FIG. 3 depicts a flowchart for a method 3000 to assess TDS levels in the MRU and treat the MRU to reduce the TDS levels. In step 3100, a geochemical assessment is performed to identify the major ions and salts in the MRU. The step 3100 can include performing the method 2000.

In step 3200, the results of the geochemical assessment of step 3100 are compared to a threshold value (see discussion below). If the TDS level obtained from the step 3100 is greater than the threshold value, the subsequent steps in the method 3000 are performed. In some embodiments, the step 3200 may be repeated more than once (e.g., more than two times) prior to the subsequent steps.

In step 3300, the entire MRU 1000 is flushed with a first solution to remove neutral, monoanionic, dianionic and trianionic salt residues from the MRU 1000, such as from the inlet and flow lines within the MRU. The first solution is an aqueous solution with sodium bicarbonate (NaHCO$_3$). In some embodiments, the first solution has a pH of at least 4.8 (e.g., at least 4.9, at least 5.0, at least 5.1, at least 5.2) and/or at most 5.3 (e.g., at most 5.2, at most 5.1, at most 5.0, at most 4.9). In some embodiments, the first solution has a concentration of sodium bicarbonate of at least 0.015 (e.g., at least 0.02, at least 0.025, at least 0.03, at least 0.035, at least 0.04, at least 0.045, at least 0.05, at least 0.055, at least 0.06, at least 0.065, at least 0.07, at least 0.075, at least 0.08, at least 0.085, at least 0.09, at least 0.095) M and/or at most 0.1 (e.g., at most 0.095, at most 0.09, at most 0.085, at most 0.08, at most 0.075, at most 0.07, at most 0.065, at most 0.06, at most 0.055, at most 0.05, at most 0.045, at most 0.04, at most 0.035, at most 0.03, at most 0.025, at most 0.02) M. In some embodiments, the first solution is at a temperature of at least 35 (e.g., at least 40, at least 45° C.) and/or at most 50 (e.g., at most 45, at most 40° C.) In some embodiments, the first solution is at a temperature of 35° C. The step 3300 can be repeated at least twice (e.g., at least three times, at least four times, at least five times).

In step 3400, the entire MRU 1000 is flushed with a second solution to remove salts and reduce TDS levels in the MRU 1000. In certain embodiments, the second solution has a pH of at least 6.5 (e.g., at least 6.6, at least 6.7, at least 6.8, at least 6.9, at least 7, at least 7.1, at least 7.2, at least 7.3, at least 7.4, at least 7.5, at least 7.6, at least 7.7, at least 7.8, at least 7.9, at least 8, at least 8.1, at least 8.2, at least 8.3, at least 8.4, at least 8.5, at least 8.6, at least 8.7, at least 8.8, at least 8.9, at least 9.0, at least 9.1, at least 9.2, at least 9.3, at least 9.4, at least 9.5, at least 9.6, at least 9.7, at least 9.8, at least 9.9, at least 10, at least 10.1, at least 10.2) and/or at most 10.3 (e.g., at most 10.2, at most 10.1, at most 10, at most 9.9, at most 9.8, at most 9.7, at most 9.6, at most 9.5, at most 9.4, at most 9.3, at most 9.2, at most 9.1, at most 9, at most 8.9, at most 8.8, at most 8.7, at most 8.6, at most 8.5, at most 8.4, at most 8.3, at most 8.2, at most 8.1, at most 8, at most 7.9, at most 7.8, at most 7.7, at most 7.6, at most 7.5, at most 7.4, at most 7.3, at most 7.2, at most 7.1, at most 7, at most 6.9, at most 6.8, at most 6.7, at most 6.6). In certain embodiments, the second solution is freshwater. In certain embodiments, the second solution is at a temperature of at least 35 (e.g., at least 40, at least 45° C.) and/or at most 50 (e.g., at most 45, at most 40° C.) In certain embodiments, the second solution contains $NaHCO_3/Na_2CO_3$ buffer. In certain embodiments, the second solution contains 0.3 M $NaHCO_3/$0.7M $Na_2CO_3$ buffer. The step 3400 can be repeated at least twice (e.g., at least three times, at least four times, at least five times).

In general, the steps 3300 and 3400 are performed until the monitored TDS go below a designated specification. The amount of times the steps 3300 and 3400 are performed may be influenced by the TDS and other contaminant levels in the MRU 1000.

After implementation of the method 3000, the TDS levels of the samples should be below the threshold values from the step 2410. The steps 3300 and 3400 can be repeated (e.g., at least twice, at least three times, at least four times, at least five times) until a desired TDS level is reached. This can be assessed using the method 2000 after the method 3000 is performed.

In some embodiments, the threshold value for the rich MEG stream 1002 in the step 3200 is at least (e.g., at least 12,000, at least 12,500, at least 13,000, at least 13,500, at least 14,000, at least 14,500, at least 15,000, at least 15,500) mg/L and/or at most 16,000 (e.g., at most 15,500, at most 15,000, at most 14,500, at most 14,000, at most 13,000, at most 12,500) mg/L. Without wishing to be bound by theory, it is believed that this TDS level varies from system to system and is dependent on the capacity of the MEG filtration unit and the amount of natural gas produced per day.

In some embodiments, the threshold value for the lean MEG stream 1042 in the step 3200 is at least 15700 (e.g., at least 15713, at least 16000, at least 17000, at least 18000, at least 19000, at least 20000, at least 21000, at least 22000, at least 23000, at least 24000) mg/L and/or at most 25000 (e.g., at most 24000, at most 23000, at most 22000, at most 21000, at most 19000, at most 18000, at most 17000, at most 16000) mg/L.

In some embodiments, if the TDS level of the lean MEG stream 1042 are consistently above the desired specification (at least 15700 mg/L and/or at most 25000 mg/L), the method 3000 can be used.

Figure 4:
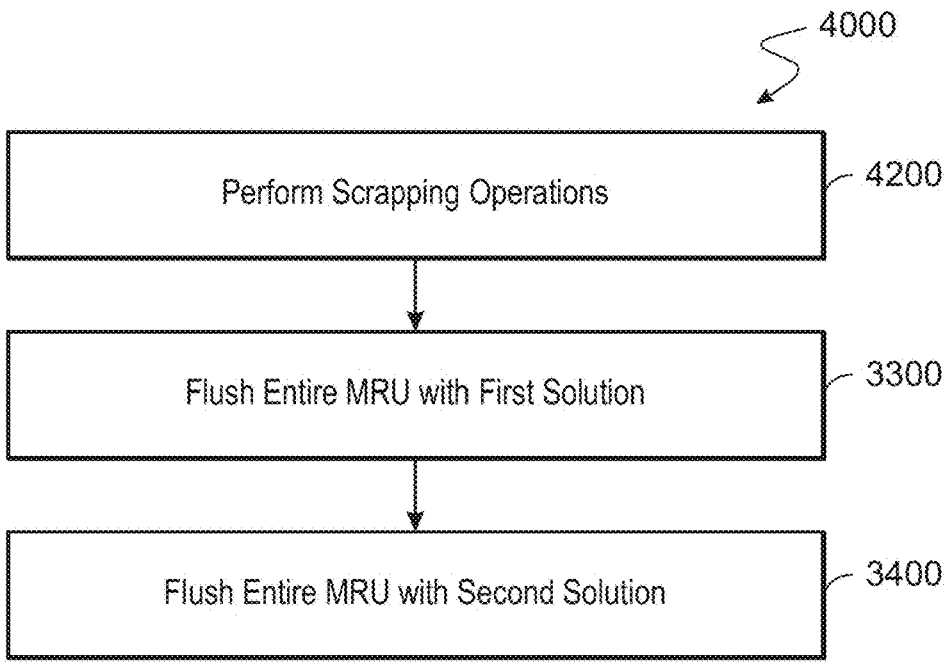
FIG. 4 depicts a flowchart of a method.

In certain embodiments, if the TDS level of the lean MEG stream 1042 is above the MRU 1000 designated specification, the method 3000 can be used. In certain embodiments, the MRU 1000 designated specification is at least 9500 (e.g., at least 10000, at least 10500, at least 11000, at least 11500, at least 12000, at least 12500, at least 13000, at least 13500, at least 14000, at least 14500, at least 15000, at least 155000) mg/L and/or at most 15800 (e.g., at most 15500, at most 15000, at most 14500, at most 14000, at most 13500, at most 13000, at most 12500, at most 12000, at most 11500, at most 11000, at most 10500, at most 10000) mg/L FIG. 4 depicts a flowchart for a method 4000 to treat the MRU 1000 to reduce the TDS levels. The method 4000 can be performed if relatively high TDS levels cause excessive salt deposits in the MRU 1000, causing shutdowns. Without wishing to be bound by theory, it is believed that shutdowns can occur when the MEG filtration systems (e.g., candle filters) in the MRU 1000 are blocked by excessive salt deposits. The MRU 1000 would be shutdown to replace the filters.

In the step 4200, mechanical scrapping operations are performed to remove residual salt deposited on a surface of the MRU 1000 and/or a flow lines. The scrapping operations includes the use of a mechanical scrapping tools to remove precipitated salts and sand debris from the trunklines that are connected to the wellhead and sludge catcher. The mechanical scrapping tool can include an automatic metal scraping brush (a crimped wire brush). The flow line can be a flow line establishing fluid communication between the wellhead and the MRU. The mechanical scrapping operations can be performed on the topside of the sludge catcher and trunk lines to remove residual salt deposited at the flow lines. The topside of the sludge catcher refers to the trunk lines that are connect the wellhead and sludge catcher.

In the step 3300, the entire MRU 1000 is flushed with a first solution (see discussion above). The step 3300 can be repeated at least twice (e.g., at least three times, at least four times, at least five times).

In the step 3400, the entire MRU 1000 is flushed with a second solution. In some embodiments, the second solution contains $NaHCO_3/Na_2CO_3$ buffer solution. In some embodiments, the second solution contains 0.3 M $NaHCO_3/0.7M$ $Na_2CO_3$ buffer. In some embodiments, the second solution has a pH of 10.3 (see discussion above). The step 3400 can be repeated at least twice (e.g., at least three times, at least four times, at least five times).

In some embodiments, if TDS in the lean MEG stream 1042 is consistently at least 50,000 mg/L and/or at most 80,000 mg/L after changing the candle filters and/or using the method 3000, the method 4000 is implemented.

In some embodiments, when the TDS levels of the lean MEG output from the reclamation section 1020 (the stream 1022) exceed 120000 mg/L, the method 4000 can be used.

For organic cross contamination or condensate carryover management and treatment, lean MEG and corrosion inhibitor dosing going in and out of the MRU 1000 can be monitored to establish a quality control step to determine the onset of high TDS and salts contamination levels. Based on the measurements, contaminated MEG may be replaced with fresh MEG as appropriate during periods of severe MEG contamination from organics and/or condensate carryover. In general, TDS and organic contaminants measurements should be conducted for both the inlet and outlet streams of the MRU 1000 (the streams 1002 and 1042). In certain embodiments, fresh MEG is used to replace contaminated MEG when the TDS levels in the stream 1002 are at least 100000 (e.g., at least 110000, at least 120000, at least 130000, at least 140000) mg/L and/or at most 150000 (e.g., at most 140000, at most 130000, at most 1200000, at most 100000) mg/L. In certain embodiments, fresh MEG is used to replace contaminated MEG when the stream 1002 has an amount of organic compounds of at least 25 (e.g., at least 50, at least 75) ppm and/or at most 100 (e.g., at most 75, at most 50) ppm.

9

Dual Multi-Cascade Filtration System

Figure 5:
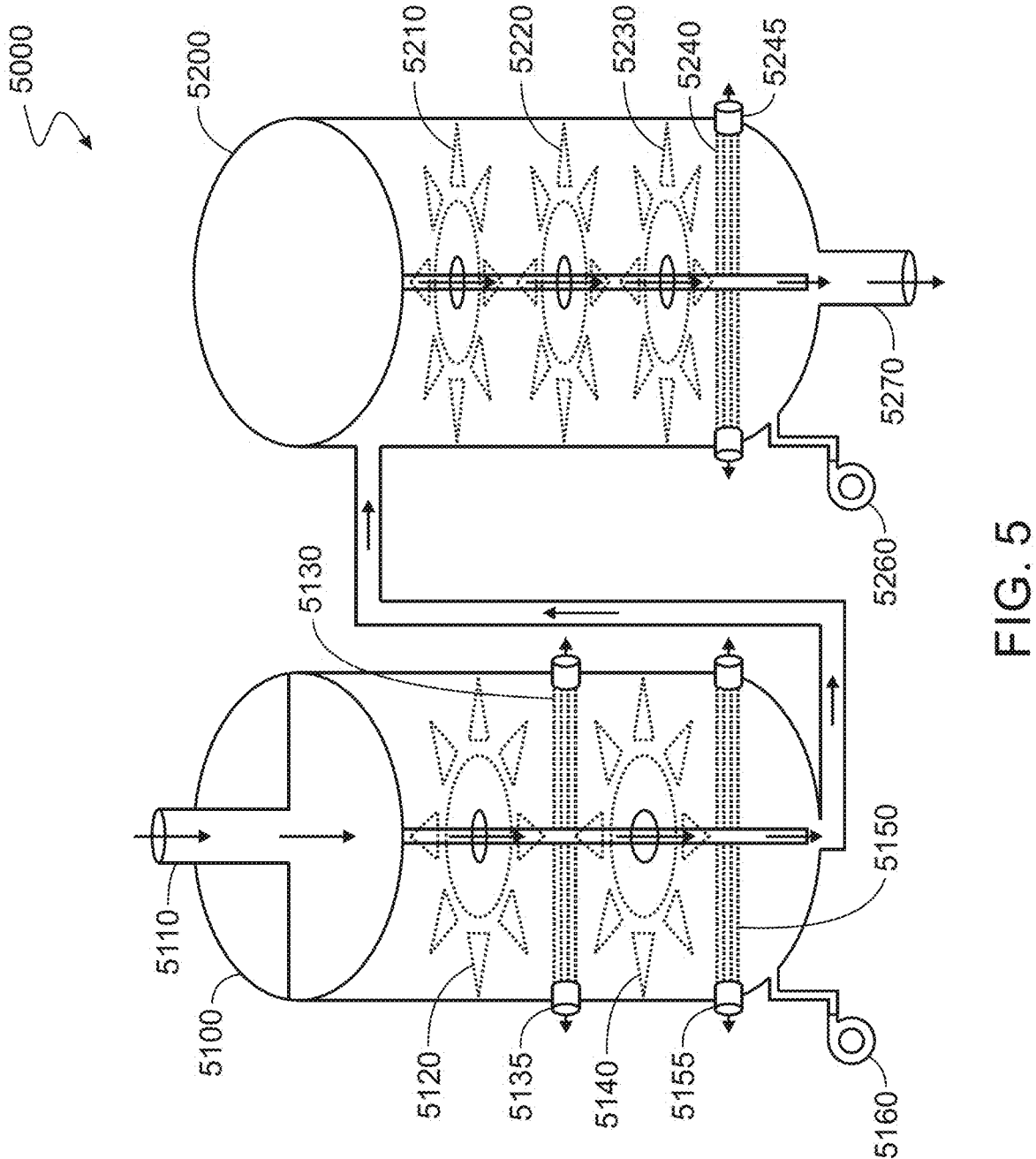
FIG. 5 depicts a schematic of a system.

FIG. 5 depicts a schematic for a dual multi-cascade filtration (DMCF) system 5000. The DMCF system 5000 can be used in alternative to or in addition to the methods 3000 or 4000 to reduce TDS levels when relatively high TDS levels are present in the MRU 1000. For example, the DMCF system 5000 can be used when a TDS level consistently stays above 100,000 mg/L in the reclamation section 1020 and/or the regeneration section 1040.

The DMCF system 5000 can be used with the methods 3000 or 4000 if salt levels in the MRU continue to increase. Without wishing to be bound by theory, it is believed that the first solution in the step 3300 can solubilize the salts relatively easily, for subsequent removal from the MRU.

A MEG-containing stream enters a first section 5100 via an inlet 5110. In the first section 5100, the stream passes through a thermal cyclic filter 5120, followed by a first porous membrane filter 5130, a thermal cyclic filter 5140 and a second porous membrane filter 5150. A vacuum pump 5160 maintains the first section 5100 at a relatively low pressure (e.g., under vacuum). In some embodiments, the first section 5100 is maintained at a pressure of at least 15 (e.g., at least 16, at least 17, at least 18, at least 19, at least 20, at least 21) bar and/or at most 22 (e.g., at most 21, at most 20, at most 19, at most 18, at most 17, at most 16) bar.

The MEG-containing stream then passes to the second section 5200. In the second section 5200, the MEG-containing stream passes through thermal cyclic filters 5210, 5220 and 5230, then the third porous membrane filter 5240. A vacuum pump 5260 maintains the second section 5200 at a relatively low pressure (e.g., under vacuum). In some embodiments, the second section 5200 is maintained at a pressure of at least 30 (e.g., at least 35, at least 40, at least 50) bar and/or at most 55 (e.g., at most 50, at most 45, at most 40, at most 35) bar. The MEG-containing stream exits the second section 5200 via the outlet 5270.

Without wishing to be bound by theory, it is believed that DMCF system 5000 filters the salts based on size. The first section 5100 removes organic contaminants and large micron size particles and the second section 5200 removes small micron size particles. The first section 5100 and the second section 5200 are maintained under different vacuum pressures.

The first porous membrane filter 5120 has pore sizes of 50 (e.g., at least 55, at least 60, at least 65, at least 70, at least 75, at least 80, at least 85, at least 90, at least 95) μm to 100 (e.g., at most 95, at most 90, at most 85, at most 80, at most 75, at most 70, at most 65, at most 60, at most 55) μm. The second porous membrane filter 5150 has pore sizes of 5 (e.g., at least 10, at least 15, at least 20, at least 25, at least 30, at least 35, at least 40, at least 45) μm to 50 (e.g., at most 45, at most 40, at most 35, at most 30, at most 25, at most 20, at most 15, at most 10) μm.

The third porous membrane filter 5240 has pore sizes of 0.1 (e.g., at least 0.5, at least 0.1, at least 0.15, at least 0.2, at least 0.25, at least 0.3, at least 0.35, at least 0.4) μm to 0.45 (e.g., at most 0.4, at most 0.35, at most 0.3, at most 0.25, at most 0.2, at most 0.15) μm.

The first, second and third porous membrane filters 5130, 5150 and 5240, each have salt outlets 5135, 5155 and 5245, respectively, that allow for the removal of salt captured by the filters from the DMCF system 5000.

The DMCF system 5000 is a gravity and pressure-driven membrane filtration system. Without wishing to be bound by theory, it is believed that the thermal cyclic filters 5120, 5140, 5210, 5220 and 5230 remove large debris and organic contaminants via evapo-filtration and the three-stage sequential speed vacuum and membrane filtration with the first, second and third porous membrane filters 5130, 5150 and 5240 reduce the TDS level and remove inorganic salt particles from the MEG-containing stream. Without wishing to be bound by theory, it is believed that separation of the organic contaminants from the salts can enhance the salt filtration and also increase the lifetime of the first, second and third porous membrane filters 5130, 5150 and 5240. Without wishing to be bound by theory, it is believed the DMCF system 5000 can be used for the treatment of both inorganic and organic contaminants, thereby reducing (e.g., preventing) issues associated with inorganic salts and organic cross-contamination in the MRU 1000. The DMCF system has relatively high throughput and filtration thereby reducing (e.g., preventing) system shutdowns. The DMCF system 5000 can be relatively easy to operate and have relatively low operational and maintenance costs relative to certain other filtration systems.

The DMCF system 5000 can provide longer use and lifetime of MEG relative to certain other filtration systems.

Figure 6:
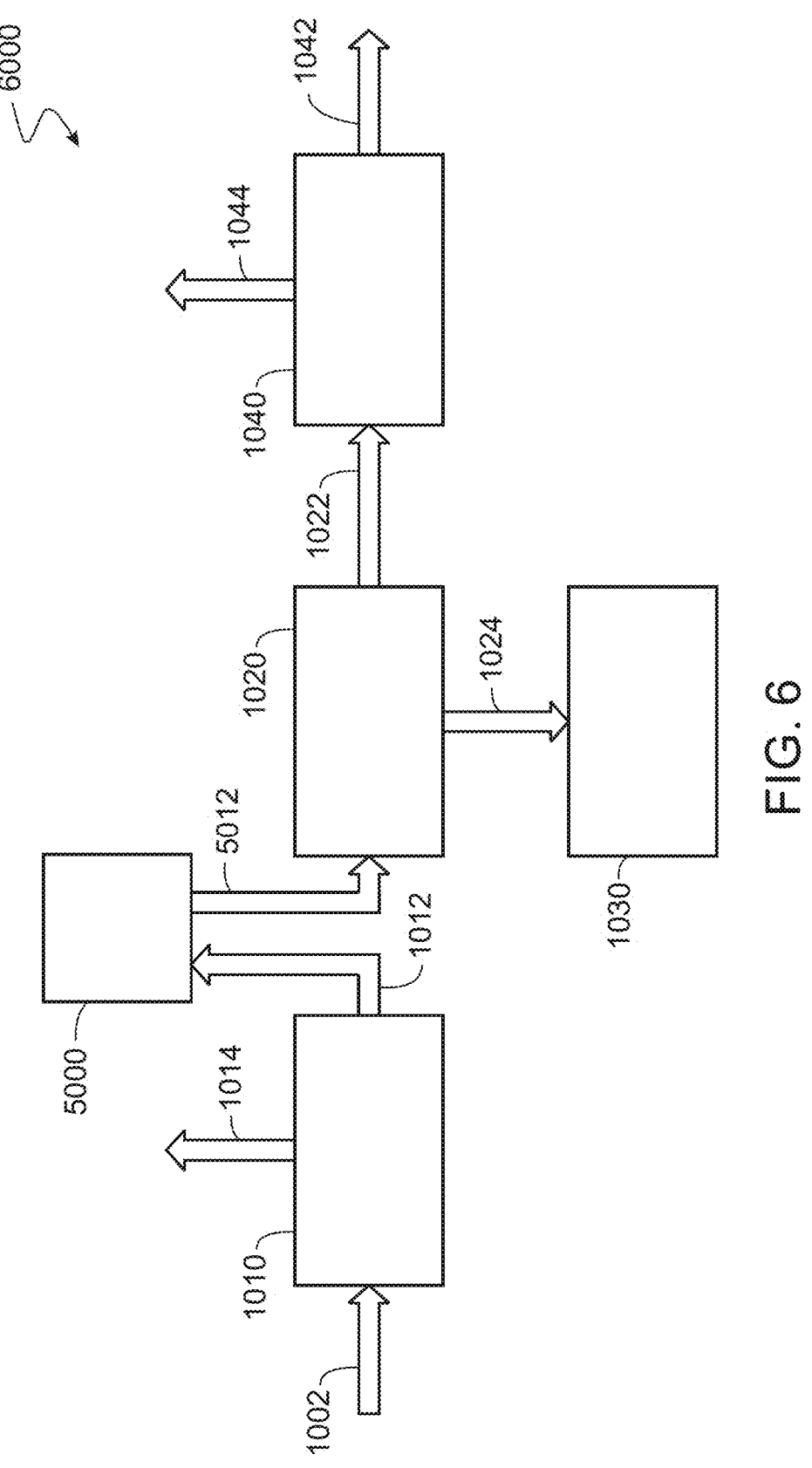
FIG. 6 depicts a schematic of a system.
Figure 8A:
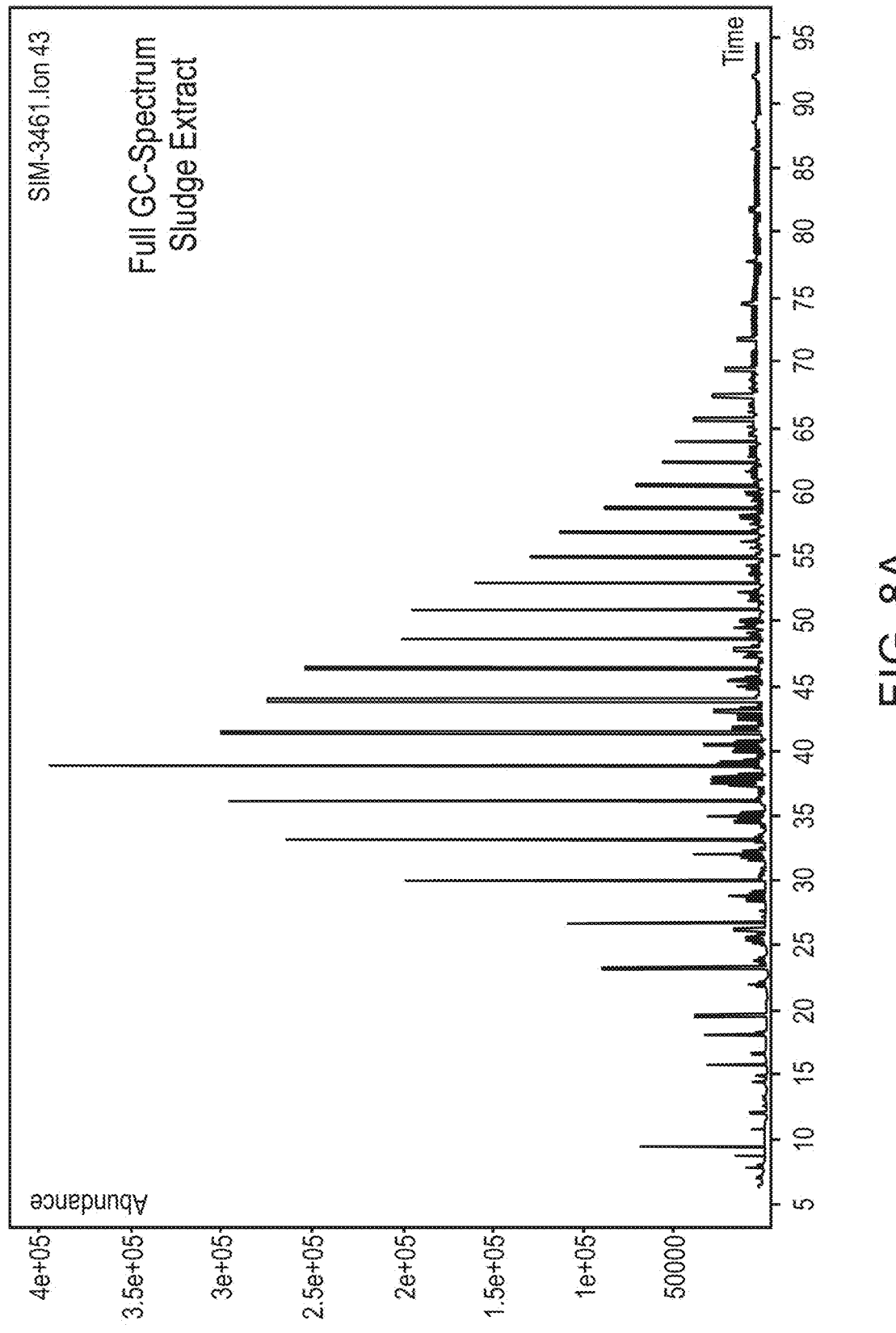
FIGS. 8A-8I depict graphs of gas chromatography mass spectrometry (GC-MS) results.
Figure 8B:
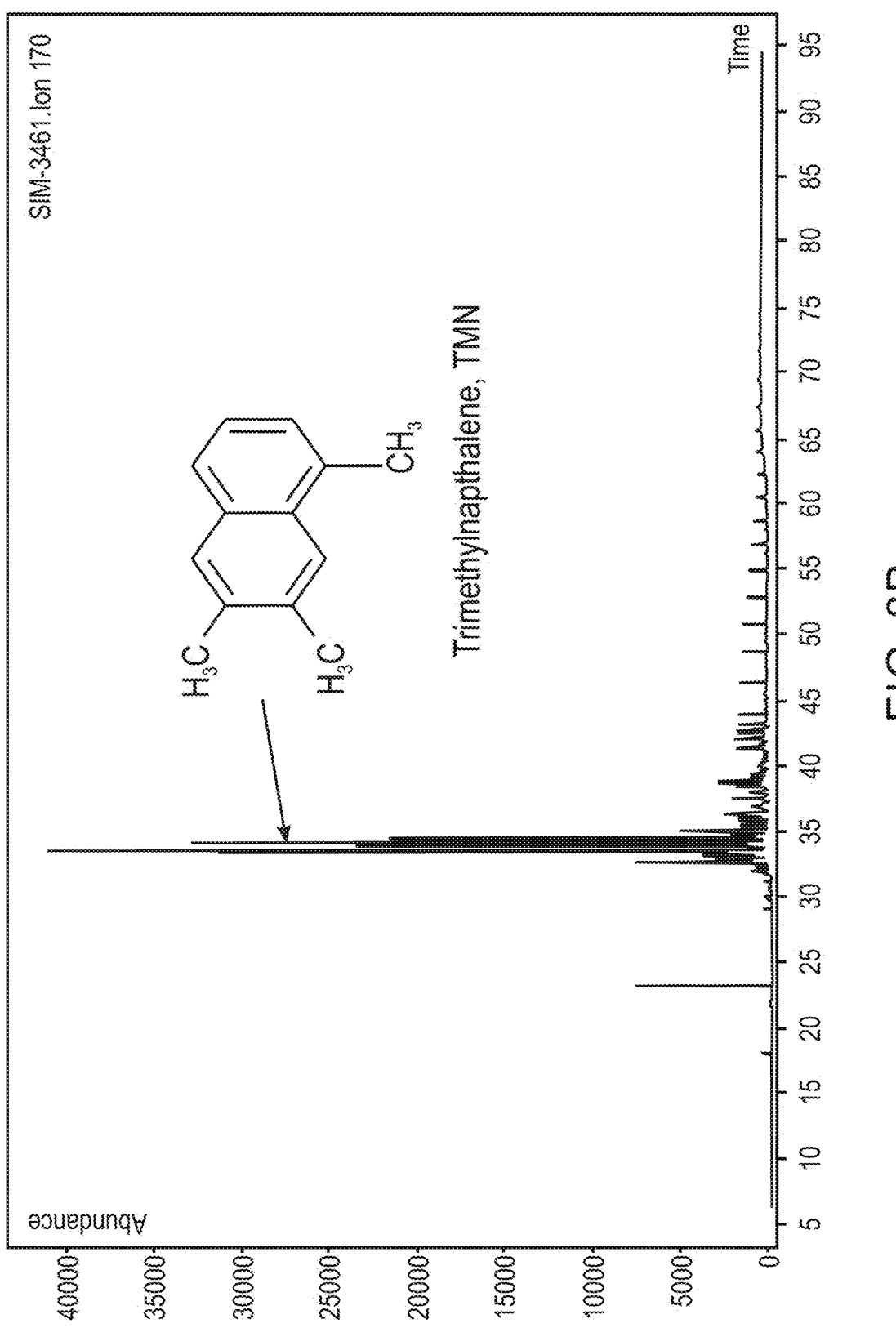
Figure 8C:
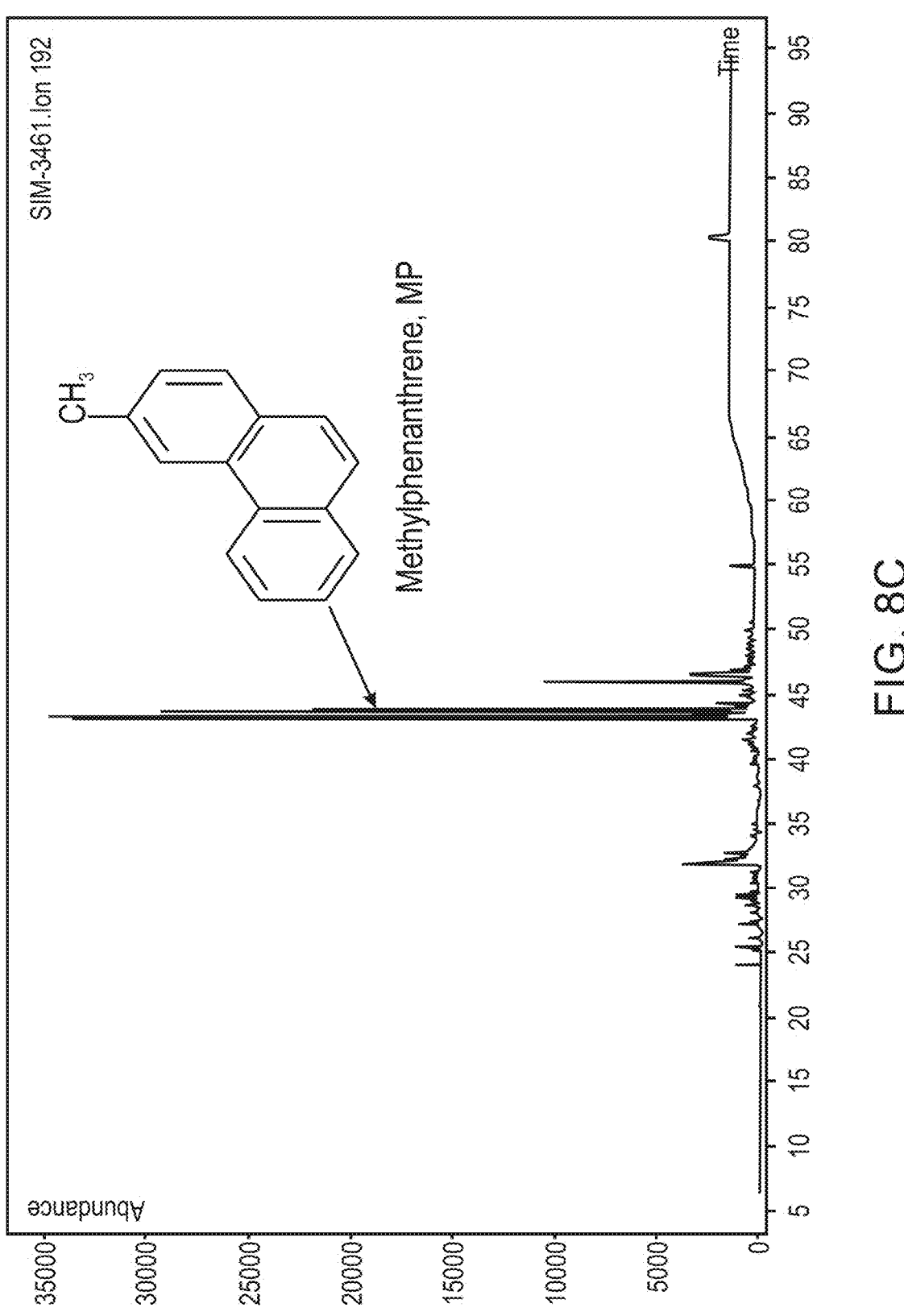
Figure 8D:
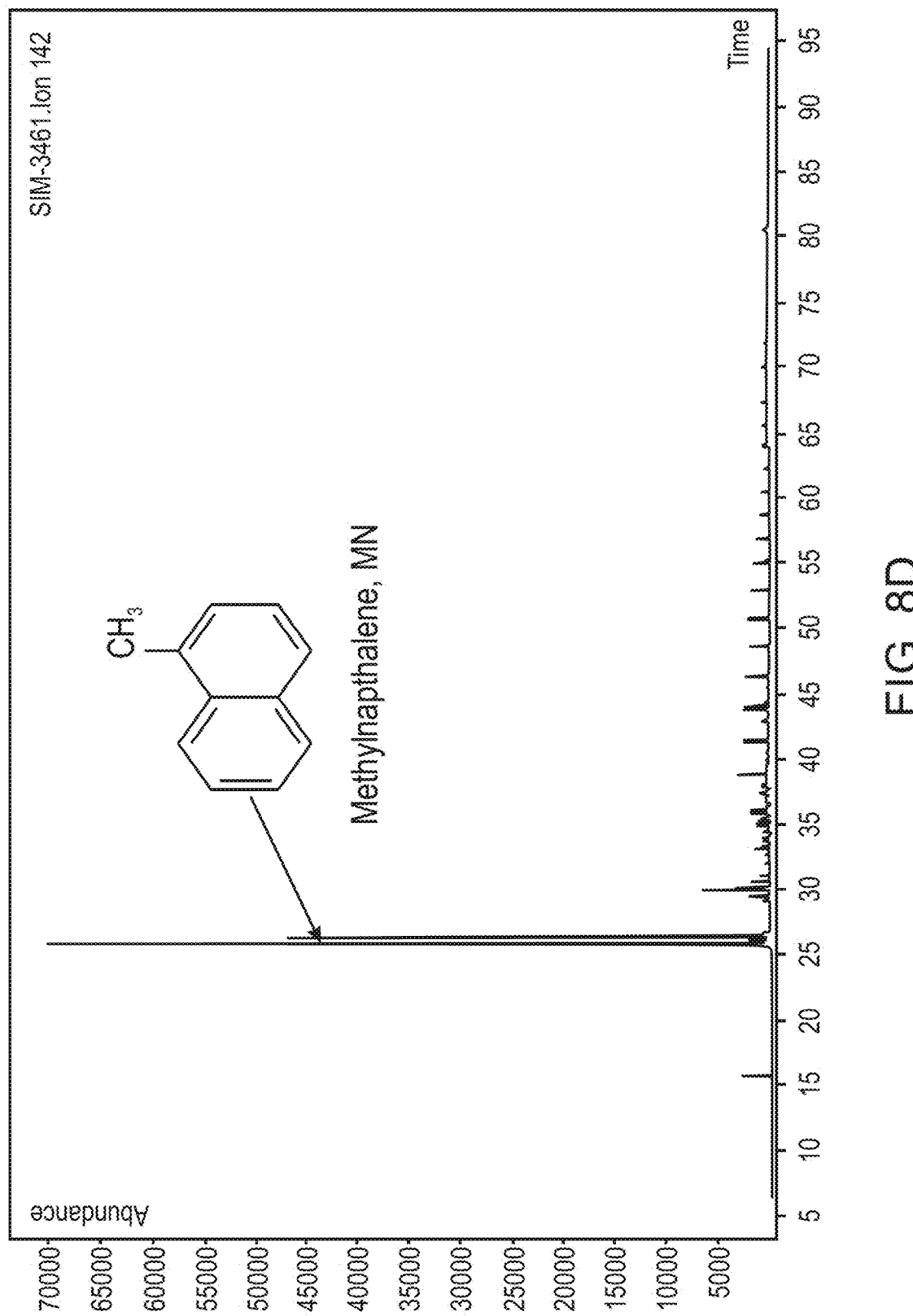
Figure 8E:
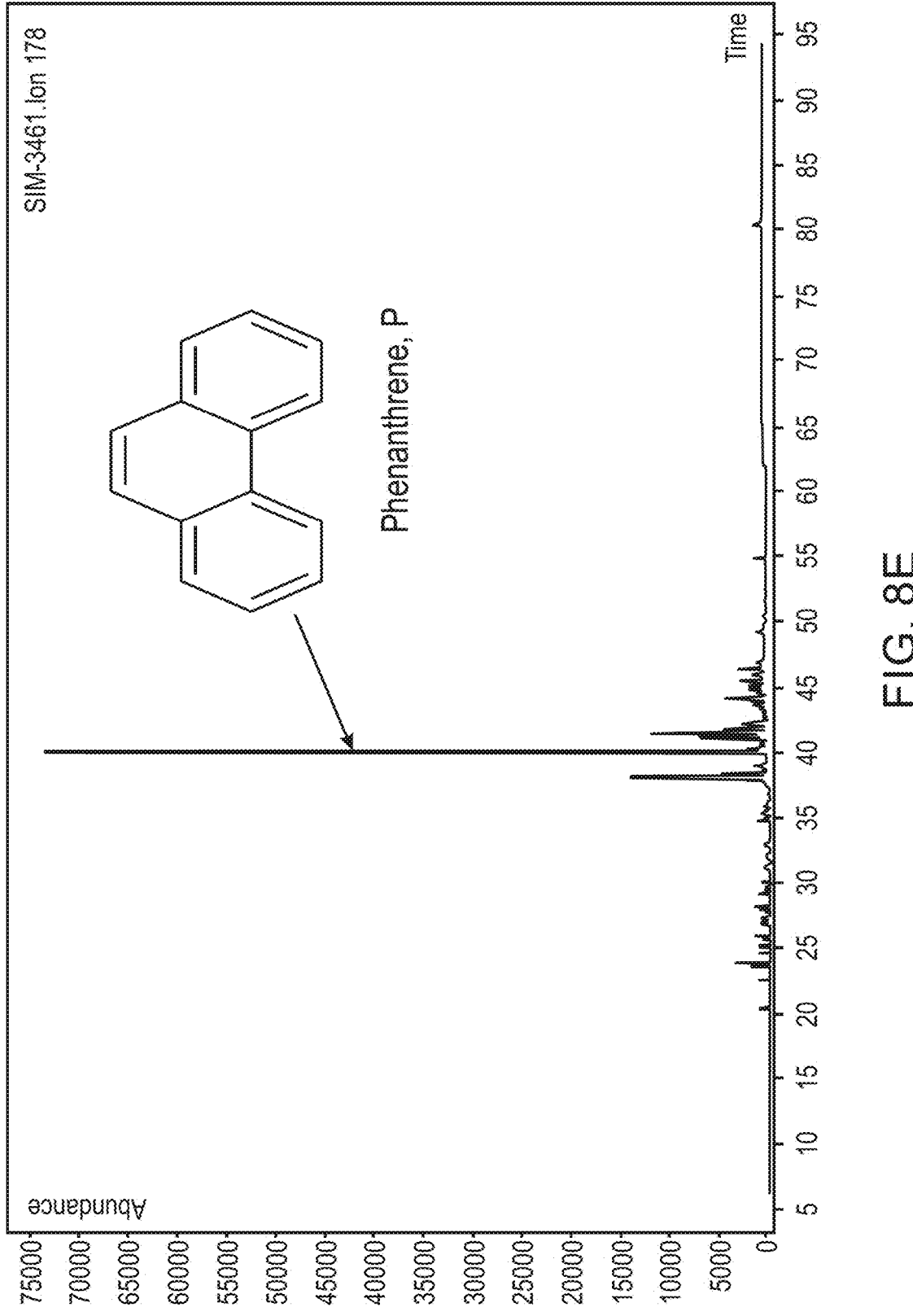
Figure 8F:
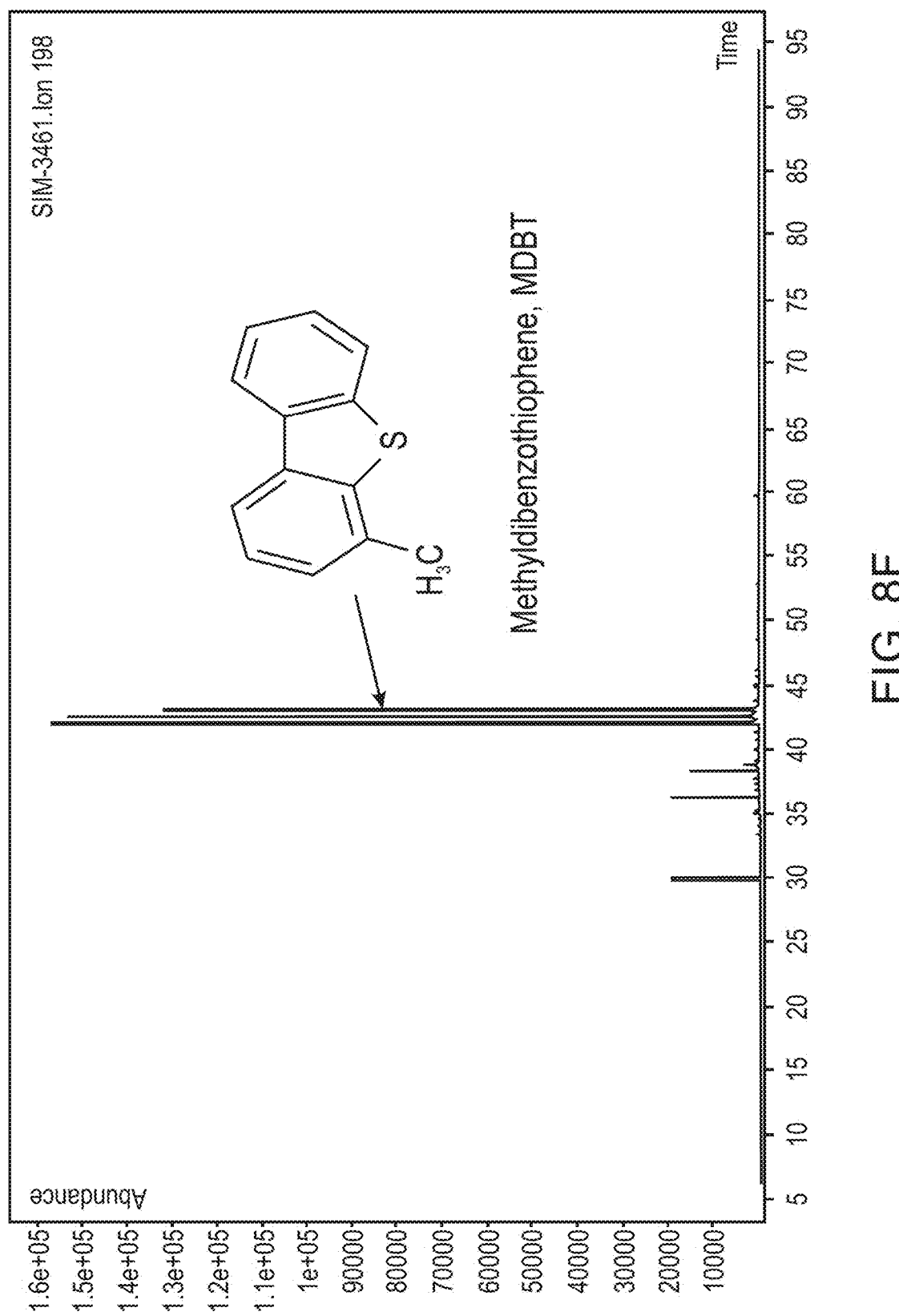
Figure 8G:
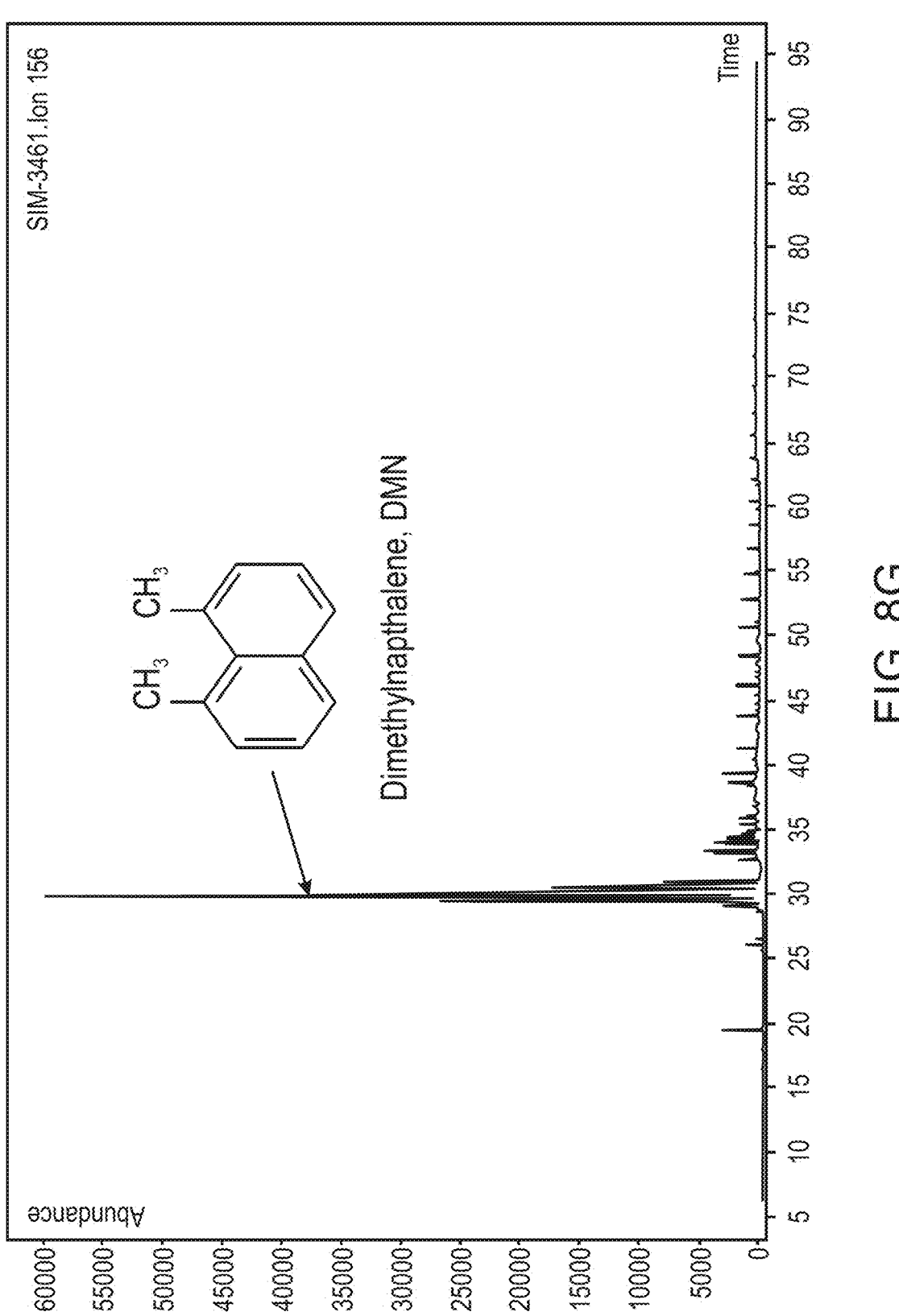
Figure 8H:
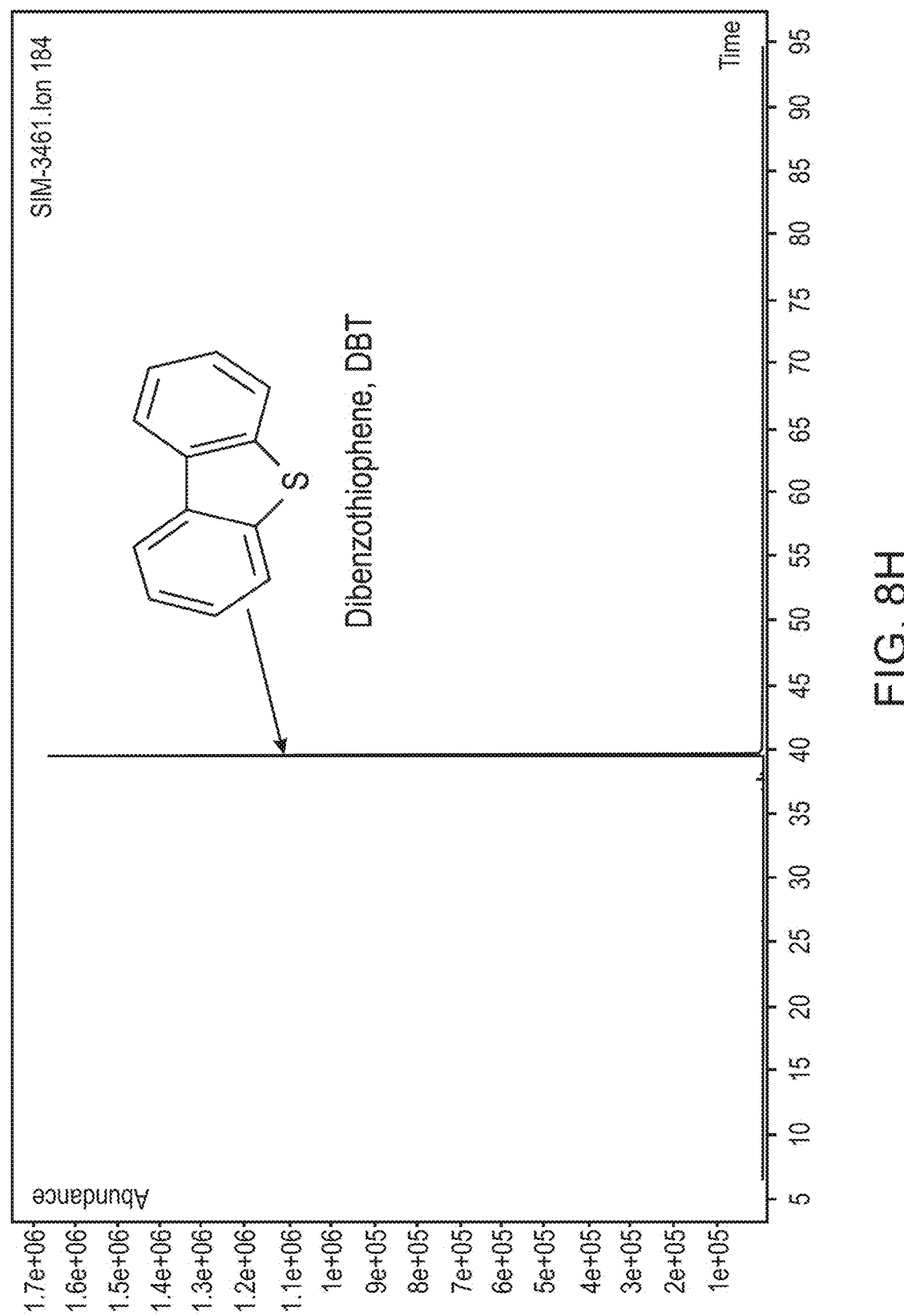
Figure 8I:
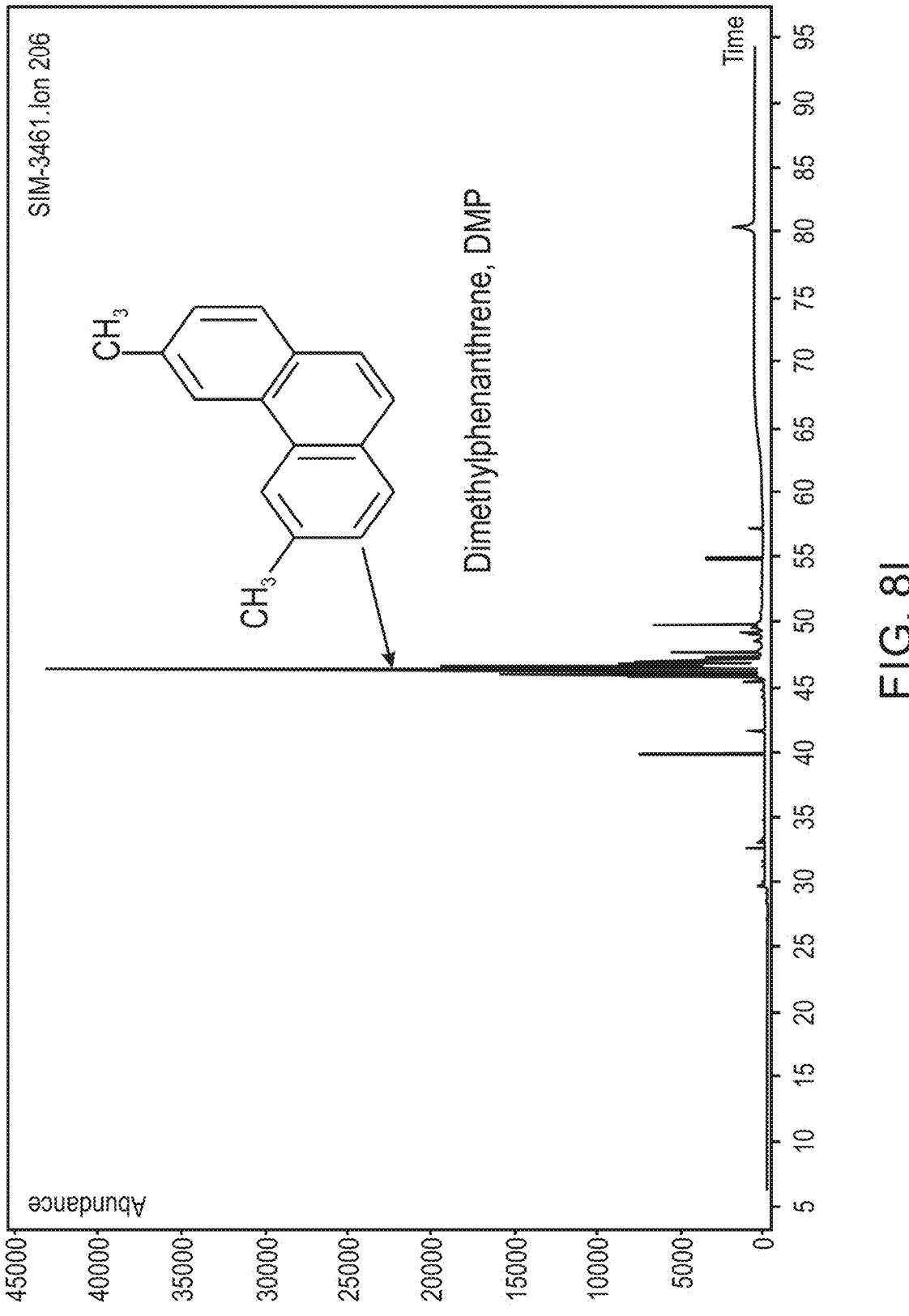

FIG. 6 depicts a schematic of a system 6000. The system 6000 includes the components of the MRU 1000 as well as the DMCF system 5000, which is used to reduce the concentration of salts and/or organic contaminants in the stream 1012, prior to entry into the reclamation section 1020. In the system 6000, rather than passing directly to the reclamation section 1020, the stream 1012 enters the DMCF system 5000. The stream 5012 exits the DMCF system 5000 and enters the reclamation section 1020. A salt and/or organic contaminant content of the stream 5012 is reduced relative to the stream 1012. In some embodiments, the TDS level of the stream 5012 is at most 12712 mg/L.

EXAMPLES

Example 1

Aqueous geochemical analyses were performed on samples from a wellhead and streams from different sections for a MRU in a natural gas plant. The streams from the MRU were a rich MEG inlet section stream (the stream 1002), a rich MEG regeneration section stream (the stream 1022), and a lean MEG reclamation section stream (the stream 1012).

Barium ($Ba^{2+}$), calcium ($Ca^{2+}$), strontium ($Sr^{2+}$), magnesium ($Mg^{2+}$), sodium ($Na^+$) and potassium ($K^+$) concentrations were analyzed after acid digestion by inductively coupled plasma mass spectrometry (ICP-MS). In the acid digestion, trace metals from high TDS samples were properly extracted and recovered using mixture of concentrated $HNO_3$, HCl, and HF for 26 min with a temperatures ranging from 200-260° C. in a microwave.

Sulfate ($SO_4^{2-}$), chloride ($Cl^-$) and hydroxide (OH) concentrations were measured by a Thermo Scientific high performance Ion Chromatograph-ICS 6000 Hybrid System. $CO_3^{2-}$ and $HCO_3$ concentrations were analyzed by chemical titration using a magnetic PHS-3E pH meter with resolution of 0.01 units. Conductivity, specific gravity, and pH were measured by Thermo Orion Versa Star Benchtop Meters. The total dissolved solid (TDS) was calculated from the sum of the chemical charge balance of cations and anions present in each sample.

The results are summarized in Table 1. The results show a progressive increase in TDS levels from 4196.6 mg/L at the wellhead to 175183.5 mg/L at the lean MEG reclamation section stream of the MRU. The major cations that contributed to the relativity high TDS levels in the MRU were barium ($Ba^{2+}$), calcium ($Ca^{2+}$), strontium ($Sr^{2+}$), magnesium ($Mg^{2+}$), sodium ($Na^+$) and potassium ($K^+$). The anions present in the system were sulfate ($SO_4^{2-}$), chloride ($Cl^-$), and carbonate ($CO_3^{2-}$). The increase in TDS and other geochemical parameters (such as conductivity and specific gravity) from the wellhead to the MRU system indicates the tendency of fouling in the MRU. This adversely influences the process safety and can cause periodic system shutdowns of the MRU.

Further mineralogical and morphological characterization by XRD and ESEM for the various salts obtained from the MRU showed that the predominant inorganic salts were 72.0-97.5 wt. % Halite (NaCl), 2.5-20.0 wt. % Sylvite (KCl), 4.0 wt. % Barite ($BaSO_4$), 2.0 wt. % anhydrite ($CaSO_4$), 1.0-3.0 wt. % sodium sulfate ($Na_2SO_4$), and 1.0 wt. % albite ((Na, Ca) (Si, Al)+08). These products contributed to the total dissolve solids (TDS) and salt observed in the MRU (FIG. 7).

TABLE 1

| | | Geochemical assessment | | | |
|---|---|---|---|---|---|
| | Units | Wellhead Formation Water | Rich MEG Inlet Section (MRU) | Rich MEG Regeneration Section (MRU) | Lean MEG Reclamation Section (MRU) |
| Major Cations | | | | | |
| Barium | mg/L | 1 | 1 | 1 | 2.5 |
| Calcium | mg/L | 139 | 571 | 851.5 | 1884.5 |
| Magnesium | mg/L | 102.5 | 1109 | 2687.5 | 3719 |
| Potassium | mg/L | 87.5 | 1462.5 | 2068 | 4628.5 |
| Sodium | mg/L | 1200.5 | 16818 | 25626.5 | 54648.5 |
| Strontium | mg/L | 1.5 | 41.5 | 63 | 137 |
| Total mono/divalent cations | mg/L137 | 1532 | 20003 | 31297.5 | 65020 |
| Major Anions | | | | | |
| Sulfate | mg/L | 25 | <100 | <100 | <100 |
| Chloride | mg/L | 2656.5 | 35604.5 | 52434 | 110043.5 |
| Carbonate | mg/L | 8.1 | <20 | <20 | <20 |
| Total Anions | mg/L | 2664.6 | 35724.5 | 52554 | 110163.5 |
| Geochemical Parameters | | | | | |
| Total Dissolved Solids | mg/L | 4196.6 | 55727.5 | 83851.5 | 175183.5 |
| pH @ 25° C. | | 7.05 | 6.8 | 7.75 | 7.1 |
| Conductivity at 25° C. | µohms/cm | 5713.5 | >10000 | >10000 | >10000 |
| Specific gravity @ 60 °F. | g/mL | 1.0134 | 1.06105 | 1.0933 | 1.17725 |

Example 2

Homogenized 15 mL water samples collected from each sampling point were placed in a Speedvac evaporation system that used centrifugation, vacuum and a temperature set at 75° C. to remove water while concentrating and maintaining the salt integrity. The salts were further dried in an oven overnight at temperature of 47° C. for gravimetric analysis. Compositional and morphological characterization of the various salts obtained from the rich MEG inlet section stream, the MEG regeneration section, and a lean MEG reclamation section were analyzed by semi-quantitative X-ray powder diffraction (XRD) and environmental scanning electron microscopy (ESEM).

The results are presented in FIG. 7. The results show that, with the exception of wellhead samples, aqueous to solid phase transformation via evaporation and gravimetric analyses had significant saturation of salt products ranging from 50,370 mg/L to 159,010 mg/L. The salt measurements from the MRU were higher than the designed capacity of 15,700 mg/L. These amounts may affect the performance of the MRU.

Example 3

Rich MEG regeneration section samples containing approximately 10 wt. % precipitated salts were centrifuged for 10 minutes at 5000 rpm. The salt-containing hydrocarbon residues were collected and analyzed by TGA to determine the bulk organic and inorganic components. A subsample was placed in a continuous soxhlet extraction system and the organic components were extracted using DCM for 72 hours at 55° C. The organic components extracted with DCM was concentrated via rotary evaporation. GC-MS with selected ion monitoring was used to identify the predominant hydrocarbon contaminants.

The TGA analysis showed an average of 23.3±2.1 wt. % of free hydrocarbon/organic components and 87.7±2.1 wt. % total inorganic salt products. The GC-MS results identified the condensed phase aromatic hydrocarbon products (methylated naphthalene, phenanthrene) and other substituted aromatic sulfur analogs of benzothiophene depicted in FIGS. 8A-8I.

Without wishing to be bound by theory, it is believed that the source of the organic products may be the carryover of condensed phase chemical dosing products (e.g., corrosion inhibitors) injected into the natural gas plant unit. The formation of aromatic thiophene indicates that carryover organic products can undergo sulfurization with sulfide/bisulfide ($H_2S/HS^-$) in sour gas plants to form the corresponding thiophenes, which can potentially deposit in the MRU and exacerbate salt nucleation and aggregation processes.

Example 4

In a pilot scale TDS treatment experiments, the entire MRU system (from the inlet, trunkline and flow lines) was flushed twice with a first solution with 0.1 M $NaHCO_3$ of pH of 8.5 at 35° C. The MRU system was then flushed three times freshwater with a pH of 6.7. The entire procedure was repeated twice and a TDS level of 15713 mg/L in the lean MEG stream was reached.

Example 5

A second treatment approach was studied for excessive salt deposition mitigation using a simulated flow-through MEG reactor system that was later deployed in actual MRU on the field to resolved high TDS issues. The experiment was performed in a glass flow reactor designed to mimic tendency or tests MEG fouling and treatments with different chemicals, buffer solutions, and scrapping tools. In this embodiment, multiple scrapping operations from the topside of the sludge catcher and trunk lines were performed to remove precipitated salt deposited in the flow lines.

The MRU system (from the inlet, trunkline and flow lines) was then flushed with a first a first solution twice with circumneutral pH water range ($4.8 \leq pH \leq 5.3$) with added 0.1 $NaHCO_3$ at 35° C. followed by freshwater buffer solution treatment made of 0.3 M $NaHCO_3$/0.7 M $Na_2CO_3$ to raise the pH to 10.3 at 35° C. The MRU system was then flushed three times with freshwater with a pH of 6.7.

After the procedure, TDS levels in the rich MEG in the inlet and regeneration sections and the lean MEG in reclamation units were measured as 17,238 mg/L, 16,931 mg/L, and 15,607 mg/L, respectively. A weekly geochemical assessments (step 2410) should be implemented to the TDS levels in the MRU during normal operations.

Example 6

A model DMCF system (as depicted in FIG. 5) was positioned after MEG candle filters (upstream of the reclamation and downstream of the pretreatment process of the MRU) to further remove residual salts from the MEG-containing stream. Sub-samples of the MEG-containing stream that passed through the DMCF after further treatment were periodically collected and analyzed by conductivity meter. A TDS level of 12,712 mg/L was measured.

What is claimed:

1. A method, comprising:
measuring a total dissolved solid content in a monoethylene glycol (MEG)-containing stream output from a MEG recovery unit (MRU);
comparing the measured total dissolved solid content to a threshold value; and
when the measured total dissolved solid content is above the threshold value, flushing the MRU with a first solution comprising sodium bicarbonate and having a pH of from 4.8 to 5.3.

2. The method of claim 1, wherein the first solution comprises from 0.015 M to 0.1 M sodium bicarbonate.

3. The method of claim 1, wherein a temperature of the first solution is from 35° C. to 50° C.

4. The method of claim 1, further comprising flushing the MRU with the first solution a second time.

5. The method of claim 1, further comprising, after flushing the MRU with the first solution, flushing the MRU with a second solution having a pH of from 6.5 to 10.3.

6. The method of claim 5, further comprising flushing the MRU with the second solution a second time.

7. The method of claim 1, further comprising, prior to flushing the MRU with the first solution, mechanically removing a salt deposit from a surface of a member selected from the group consisting of the MRU and a flow line in fluid communication with the MRU.

8. The method of claim 1, wherein measuring the total dissolved solid content comprises measuring concentrations of barium ($Ba^{2+}$), calcium ($Ca^{2+}$), strontium ($Sr^{2+}$), magnesium ($Mg^{2+}$), sodium ($Na^+$), potassium ($K^+$), sulfate ($SO_4^{2-}$), chloride ($Cl^-$), and carbonate ($CO_3^{2-}$) output from the MRU.

9. The method of claim 1, wherein the threshold value is at least 15700 mg/L.

10. The method of claim 1, further comprising:
passing a MEG-containing stream output from a pretreatment section of the MRU through a first thermal cyclic filter, a first porous membrane filter, a second porous membrane filter and a third porous membrane filter to form a filtered stream; and
inputting the filtered stream into a regeneration section of the MRU,
wherein:
the first porous membrane filter is downstream of the first thermal cyclic filter;
the second porous membrane filter is downstream of the first porous membrane filter; and
the third porous membrane filter is downstream of the second porous membrane filter.

11. The method of claim 10, wherein:
the first porous membrane filter has a first pore size;
the second porous membrane filter has a second pore size;
the third porous membrane filter has a third pore size;
the first pore size is larger than the second pore size; and
the second pore size is larger than the third pore size.

12. The method of claim 10, further comprising a second thermal cyclic filter and a third thermal cyclic filter, wherein:
the second thermal cyclic filter is upstream of the second porous membrane filter and downstream of the first porous membrane filter; and
the third thermal cyclic filter is upstream of the third porous membrane filter and downstream of the second porous membrane filter.

13. A method, comprising:
flushing a monoethylene glycol recovery unit (MRU) with a first solution comprising sodium bicarbonate and a pH of 4.8 to 5.3 at a temperature of 35° C. to 50° C.

14. The method of claim 13, further comprising, after flushing with the first solution, flushing the MRU with a second solution comprising a pH of 6.5 to 10.3.

15. The method of claim 13, further comprising, prior to flushing the MRU with the first solution, mechanically removing a salt deposit from a surface of a member selected from the group consisting of the MRU and a flow line in fluid communication with the MRU.

* * * * *